US008718766B2

(12) United States Patent
Wahlberg

(10) Patent No.: US 8,718,766 B2
(45) Date of Patent: May 6, 2014

(54) ACTIVITY-RESPONSIVE PACING

(71) Applicant: St. Jude Medical AB, Jarfalla (SE)

(72) Inventor: Stefan Wahlberg, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/683,741

(22) Filed: Nov. 21, 2012

(65) Prior Publication Data

US 2013/0138171 A1 May 30, 2013

Related U.S. Application Data

(60) Provisional application No. 61/580,388, filed on Dec. 27, 2011.

(30) Foreign Application Priority Data

Nov. 30, 2011 (EP) ...................................... 11191322

(51) Int. Cl.
*A61N 1/00* (2006.01)

(52) U.S. Cl.
USPC .......................................................... 607/19

(58) Field of Classification Search
USPC ............................................................ 607/19
See application file for complete search history.

(56) References Cited

U.S. PATENT DOCUMENTS

| 4,436,092 A | 3/1984 | Cook et al. |
| 4,922,907 A | 5/1990 | Hedlin et al. |
| 4,940,052 A | 7/1990 | Mann et al. |
| 5,031,615 A | 7/1991 | Alt |
| 5,040,534 A | 8/1991 | Mann et al. |
| 5,074,302 A | 12/1991 | Poore et al. |
| 5,383,473 A | 1/1995 | Moberg |
| 5,423,867 A | 6/1995 | Poore et al. |
| 5,496,352 A | 3/1996 | Renger |
| 6,466,821 B1 | 10/2002 | Pianca et al. |
| 7,016,730 B2 * | 3/2006 | Ternes ............................ 607/17 |
| 7,021,141 B1 | 4/2006 | Nilsson et al. |
| 2006/0265019 A1 | 11/2006 | Sun et al. |
| 2009/0287270 A1 | 11/2009 | Sun et al. |

FOREIGN PATENT DOCUMENTS

| EP | 0229886 B1 | 4/1993 |
| WO | 9718010 | 5/1997 |

OTHER PUBLICATIONS

Brubaker, Peter H. PhD et al., "Chronotropic Incompetence," Circulation. 2011:123-110-1020.

* cited by examiner

*Primary Examiner* — George Manuel

(57) ABSTRACT

An implantable medical device is connectable to or comprises an activity sensor and determines a current activity level of a subject based on a sensor signal from the activity sensor. A time period during which the current activity level of the subject has exceeded a threshold level is also determined. A pulse generator controller controls a pulse generator to generate pacing pulses to be applied to the subject's heart at a pacing rate that is determined based on the current activity level and the length of the time period of activity at a level exceeding the threshold level.

17 Claims, 10 Drawing Sheets

ACTIVITY-RESPONSIVE PACING

CROSS REFERENCE TO RELATED APPLICATIONS

This application claims priority from European Patent Application No. 11191322.4, filed Nov. 30, 2011, and U.S. Provisional Patent Application Ser. No. 61/580,388, filed Dec. 27, 2011.

TECHNICAL FIELD

The present embodiments generally relate to cardiac pacing, and in particular, to such cardiac pacing that is responsive to a subject's activity level.

BACKGROUND

Cardiac pacemakers are known in the art to generate and apply pacing pulses to heart failure patients. Originally such cardiac pacemakers paced the heart at a fixed rate programmed in the cardiac pacemaker by the patient's physician.

However, the human body has an automatic regulatory mechanism that increases the cardiac output when the metabolic demand is increased, such as during increased patient activity and exercise. This increased cardiac output thereby enables sufficient transport of oxygen and removal of waste products in the patient body.

Rate-adaptive cardiac pacemakers have therefore been proposed to mimic this natural regulatory mechanism of the human body. The rate-adaptive cardiac pacemakers thereby increase the pacing rate at increased levels of metabolic activity. Various solutions have been presented in order to determine an appropriate rate increase in response to the increase in metabolic activity.

U.S. Pat. No. 4,436,092 discloses an exercise-responsive cardiac pacemaker which physiologically controls the pacing rate of a heart by sensing the venous blood temperature in the right ventricle of the heart. A temperature sensor produces an output signal which is sent to an algorithm which represents the mathematical function between venous blood temperature and the heart rate in a healthy heart.

US 2006/0265019 and US 2009/0287270 disclose rate-adaptive pacemakers that dynamically adjust their pacing rate based on a change in exertion level of the patient.

WO 97/18010 discloses a rate-adaptive pacemaker that sets a pacing rate based on the amplitude of the sensor signal from an activity sensor. The pacing rate is additionally modified based on the morphology of the sensor signal in terms of the quotient between the area of the sensor signal above a baseline and the area of the sensor signal below the baseline. This morphology-based correction of the pacing rate enable differentiation between activity levels when exercising on a leveled surface, up stairs or down stairs.

There is, though, still a need for a cardiac pacing that better mimics the natural regulatory mechanism in response to patient activity and exercise.

SUMMARY

It is a general objective to enable an activity-responsive and -adaptive cardiac pacing.

This and other objectives are met by the embodiments as disclosed herein

An aspect of the embodiments defines an activity-responsive implantable medical device comprising a connector connectable to an implantable medical lead having at least one pacing electrode. The implantable medical device comprises an activity processor configured to receive a sensor signal representative of an activity level of a subject from an activity sensor and determine a current activity level of the subject based on the sensor signal. The activity processor furthermore determines a time period during which the current activity level determined based on the sensor signal has exceed a threshold level. A pulse generator is connected to the connector and configured to generate pacing pulses to be applied to the at least one connectable pacing electrode. This pulse generator is controlled by a pulse generator controller that controls the pulse generator to generate pacing pulses at a pacing rate that is determined based on the current activity level and a length of the time period of subject activity at a level exceeding the threshold level.

Another aspect of the embodiments defines an activity-responsive implantable medical device comprising a connector connectable to an implantable medical lead having at least one pacing electrode. The implantable medical device comprises a pulse generator that is connected to the connector and configured to generate pacing pulses to be applied to the at least one connectable pacing electrode. A processing unit is implemented in the implantable medical device together with a computer program product that comprises computer readable code means, which when executed by the processing unit causes the processing unit to determine a current activity level for the subject based on a sensor signal representative of an activity level of a subject and received from an activity sensor. The processing unit is also caused to determine a time period during which the current activity level has exceeded a threshold level and determine a pacing rate for the pulse generator based on the current activity level and a length of the time period of activity of the subject at a level exceeding the threshold level.

A further aspect of the embodiments defines an activity-responsive pacing method comprising recording a sensor signal representative of an activity level of a subject. The method also comprises determining a current activity level of the subject based on the sensor signal and a time period during which the current activity level has exceeded a threshold level. A target pacing rate is then determined for the subject based on the current activity level and a length of the time period during which the activity level of the subject has exceeded the threshold level.

The present embodiments enable cardiac pacing at a pacing rate that is physiologically adaptive during periods of exercise and activity.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present embodiments generally relate to cardiac pacing and in more detail to cardiac pacing that is adaptive and dependent on the activity level of a subject, preferably a mammalian subject and more preferably a human subject.

Rate-adaptive cardiac pacing is well known in the art. Generally such rate-adaptive cardiac pacing increases the heart rate above a base rate in response to an increase in the subject's activity level. Cardiac pacemakers that are rate-adaptive then generally simply switches between a base pacing rate and an increased pacing rate when the subject's activity level has increased above a preset activity threshold.

The above described prior art rate-adaptive pacemakers may work quite well during relatively short periods of activity and exercise, such as up to a few minutes. However, experimental data as presented herein indicates that during more extended periods of activity and exercise, in particular at moderate activity levels, the heart rate of the subject increases slowly over time. Thus, when a subject starts to exercise the heart rate initially increases quite rapidly to a higher level as compared to the base heart rate of the subject. However, if the subject continues to exercise at the same activity level the heart rate does not stay at the higher level but slowly increases over time. This slow increase in heart rate over time is generally much lower as compared to the initial increase in heart rate in connection with the start of the exercise.

FIGS. 6-10 are diagrams disclosing the slow increase in heart rate during prolonged levels of exercise. The results presented in FIGS. 6-10 are recorded for a healthy male subject of age 39 years, 195 cm tall and a weight of 99 kg with a pulse monitor having a sampling rate of 1 s. Each test was performed after an ordinary working day and there was minimum 24 hours of rest between the tests.

Figure 6:
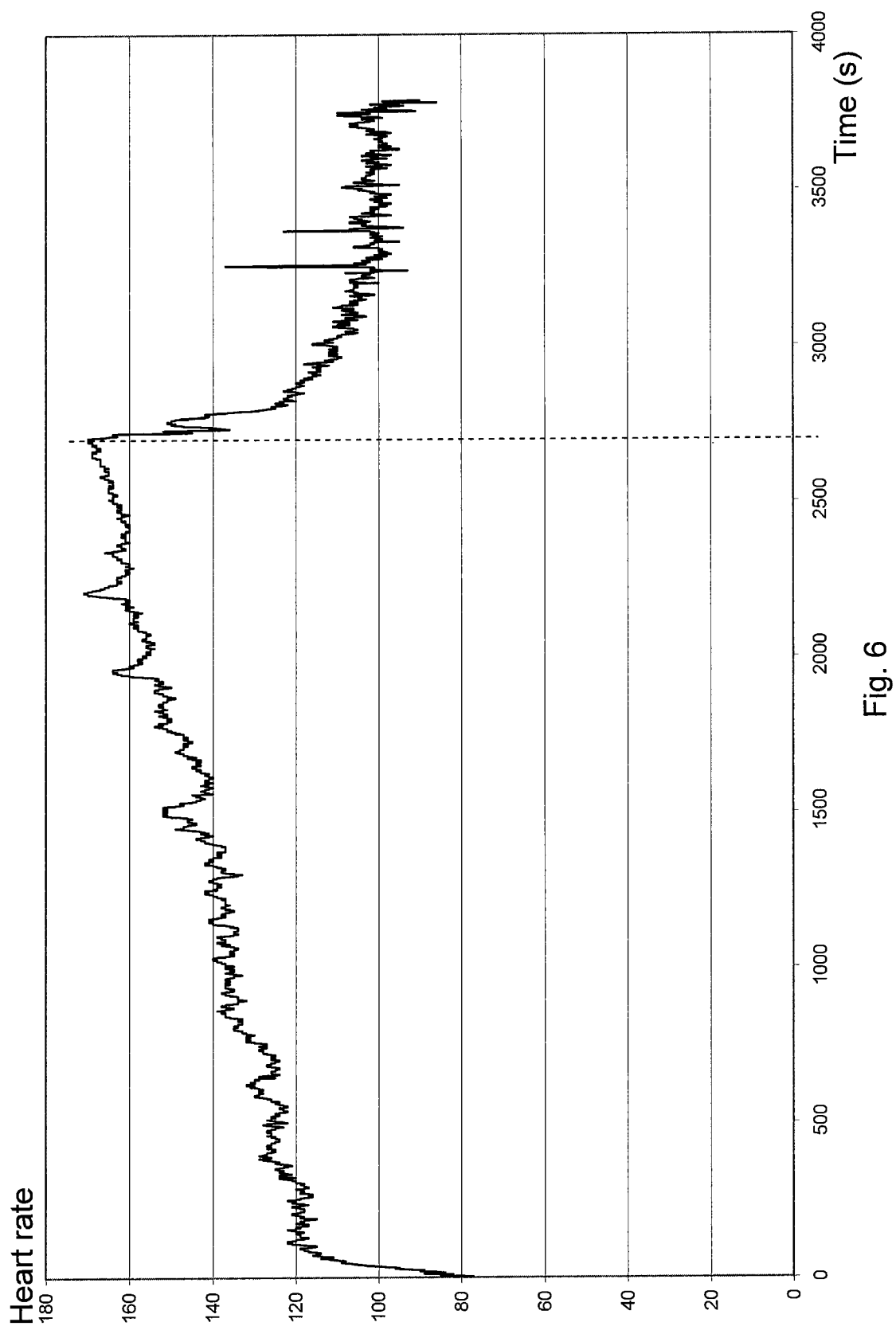
FIG. 6 is a diagram of heart rate of a human subject cycling with constant load during 45 minutes followed by slow walk during 15 minutes.

FIG. 6 illustrates the heart rate recorded during 45 minutes of cycling with constant load during 45 minutes (up to broken line) followed by slow walk during 15 minutes. As is seen in FIG. 6, at the start of the exercise the heart rate increased rapidly from a base rate of about 80 bpm (beats per minute) up to an increased level at about 120 bpm. The cardiac heart rate then slowly increased during the exercise with a linear increase of about 50 bpm up to about 170 bpm at the end of the 45 minutes of exercise. Thus, the slow increase of the heart rate was in this case about 1.1 bpm per minute during the exercise.

Further exercise and pulse monitoring tests were conducted with the same subject walking/running on a treadmill to have more control of the load as compared to the cycling test presented in FIG. 6. In these following tests three different load levels were used and are presented below in Table 1.

TABLE 1 load levels for treadmill tests

| Load | Speed (km/h) | Incline (degrees) |
|---|---|---|
| High | 6.5 | 6 |
| Low | 6.0 | 4 |
| Rest | 0 | 0 |

Figure 7:
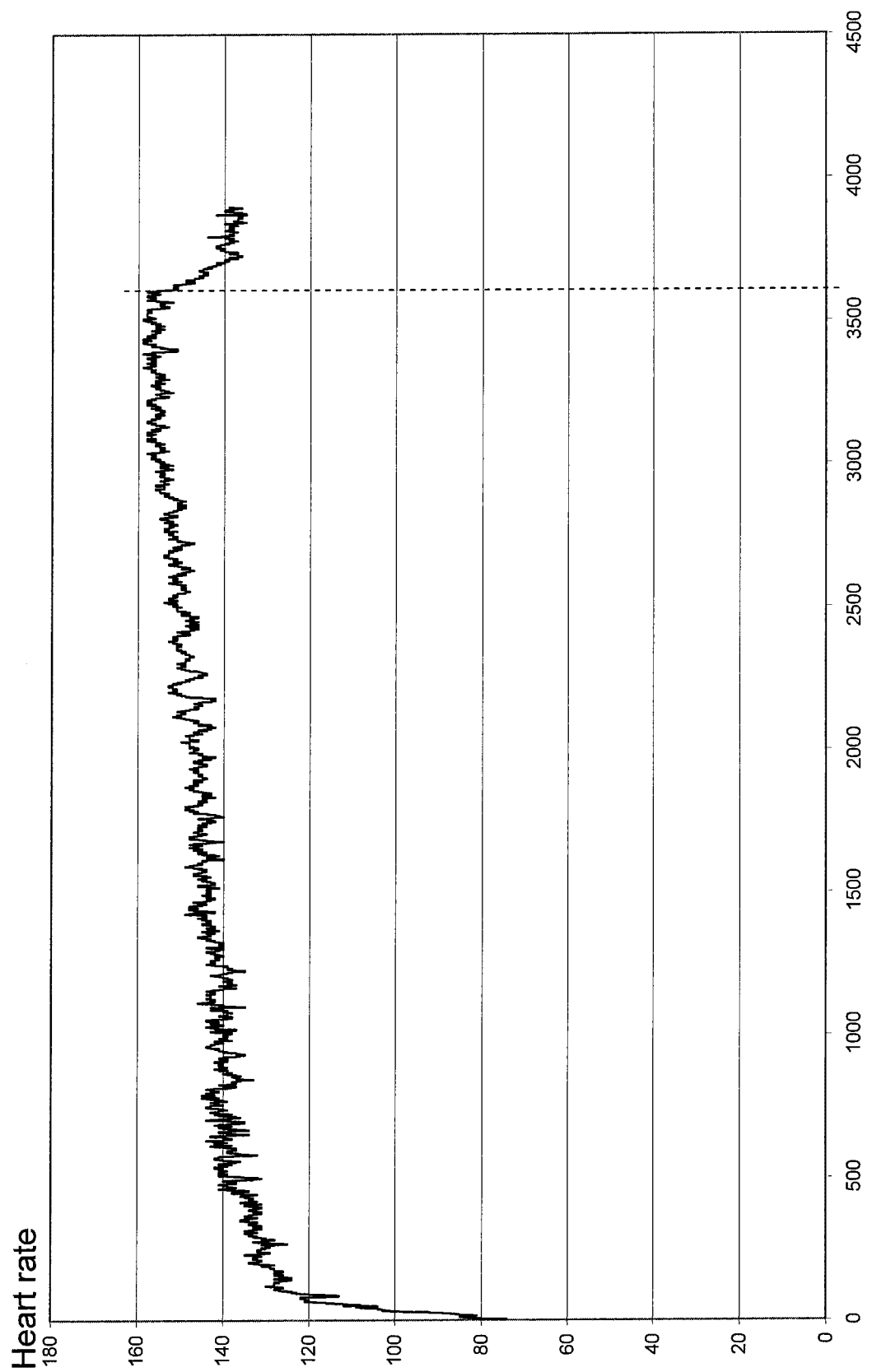
FIG. 7 is a diagram of heart rate of a human subject walking on a treadmill at a high load during 60 minutes followed by walking on the treadmill at a low load during 5 minutes.

FIG. 7 illustrates the results of a test with constant High load during 60 minutes followed by 5 minutes of Low load. As is seen in FIG. 7, within 1.5 minutes of exercise the heart rate has increased from a base rate of about 80 bpm to an increased level at about 130 bpm. After 60 minutes of exercise at load level High the heart rate has slowly and linearly increased up to about 160 bpm. Thus, this slow increase in heart rate was about 30 bpm over one hour or about 0.5 bpm/minute. When switching from load High to load Low at the end of the hour, the heart rate decreased during two minutes down to about 140 bpm. The broken line indicates the switch between High and Low load levels.

Figure 8:
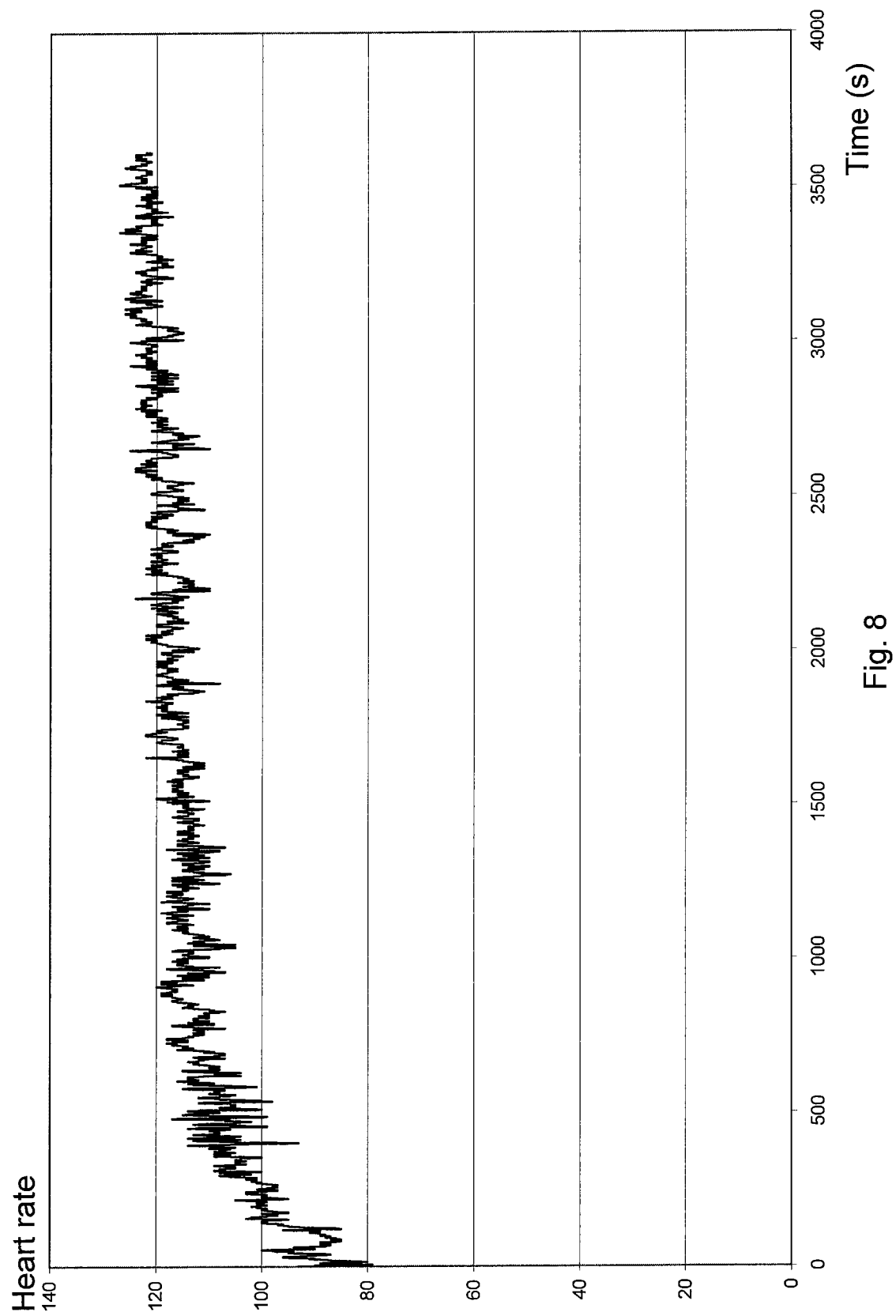
FIG. 8 is a diagram of heart rate of a human subject walking on a treadmill at low load during 60 minutes.

FIG. 8 illustrates the results of a test with constant Low load during 60 minutes. The heart rate increased from the base rate of about 80 bpm up to an increased level of about 110 bpm within the first five minutes. In this experiment it took a few minutes to adjust the load, thereby the longer time to reach steady state around 110 bpm. In this case, the heart rate increased slowly during the 60 minutes of exercise at load Low to about 120 bpm. The increase was therefore about 10 bpm over one hour or about 0.1 bpm/minute at this Low load.

Figure 9:
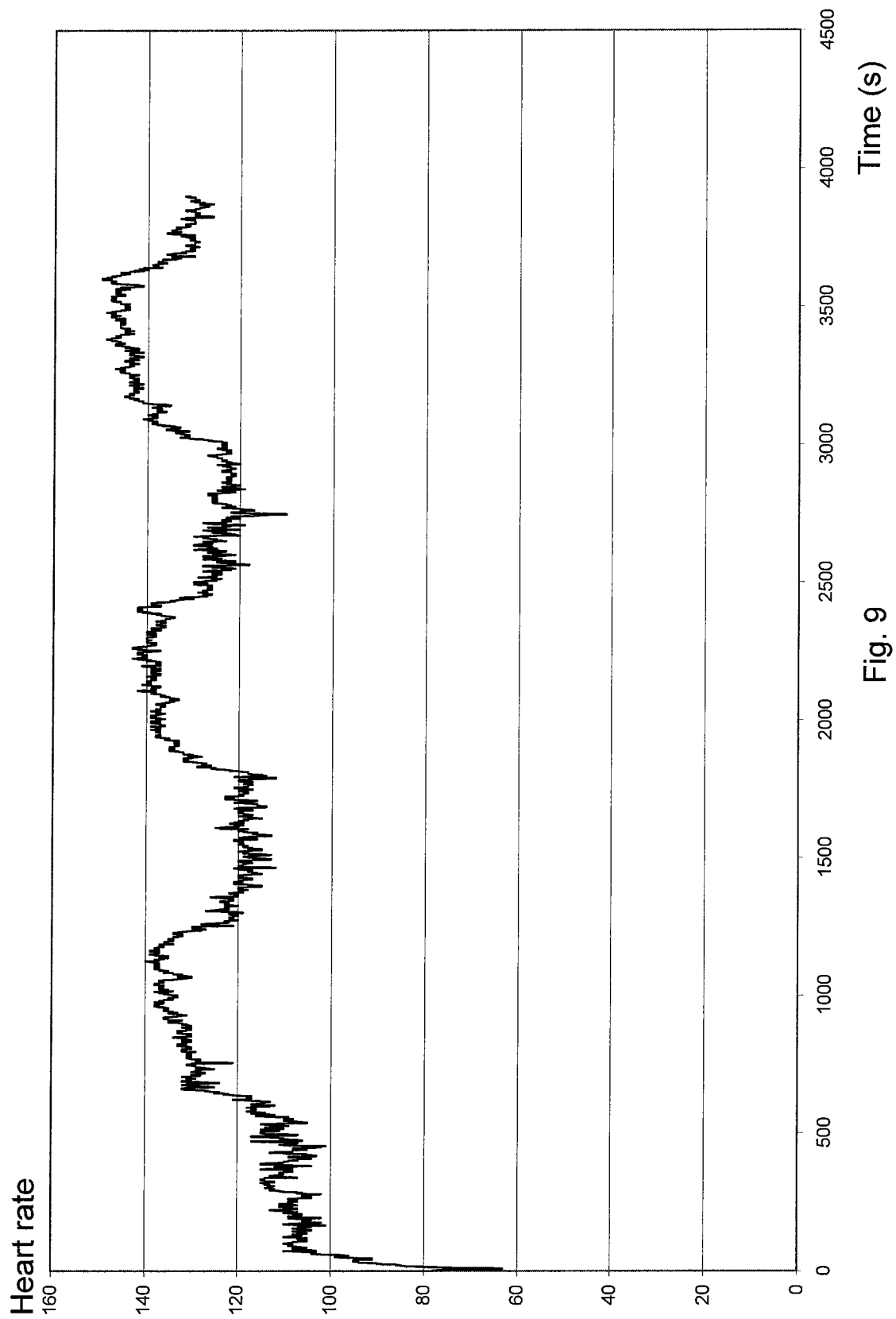
FIG. 9 is a diagram of heart rate of a human subject walking on a treadmill at alternating 10 minutes intervals of high load and low load.

FIG. 9 illustrates the results of a test combining the two load levels High and Low. This experiment was conducted in order to investigate whether the lower exercise level (Low load) between periods of higher exercise level (High load) had any impact on the heart rate curve. In these experiments the following exercise scheme was used:

0-10 minutes at load Low
10-20 minutes at load High
20-30 minutes at load Low
30-40 minutes at load High
40-50 minutes at load Low
50-60 minutes at load High As is clearly seen from FIG. 9 the heart rate in the intervals is correlated to the load level. The three higher peaks at High load have a slow linear increase in heart rate over time as have the periods of lower load (Low load). The linear increase in heart rate over time is furthermore larger at higher exercise levels (High load) as compared to the linear increase in heart rate over time during lower exercise levels (Low load).

Figure 10:
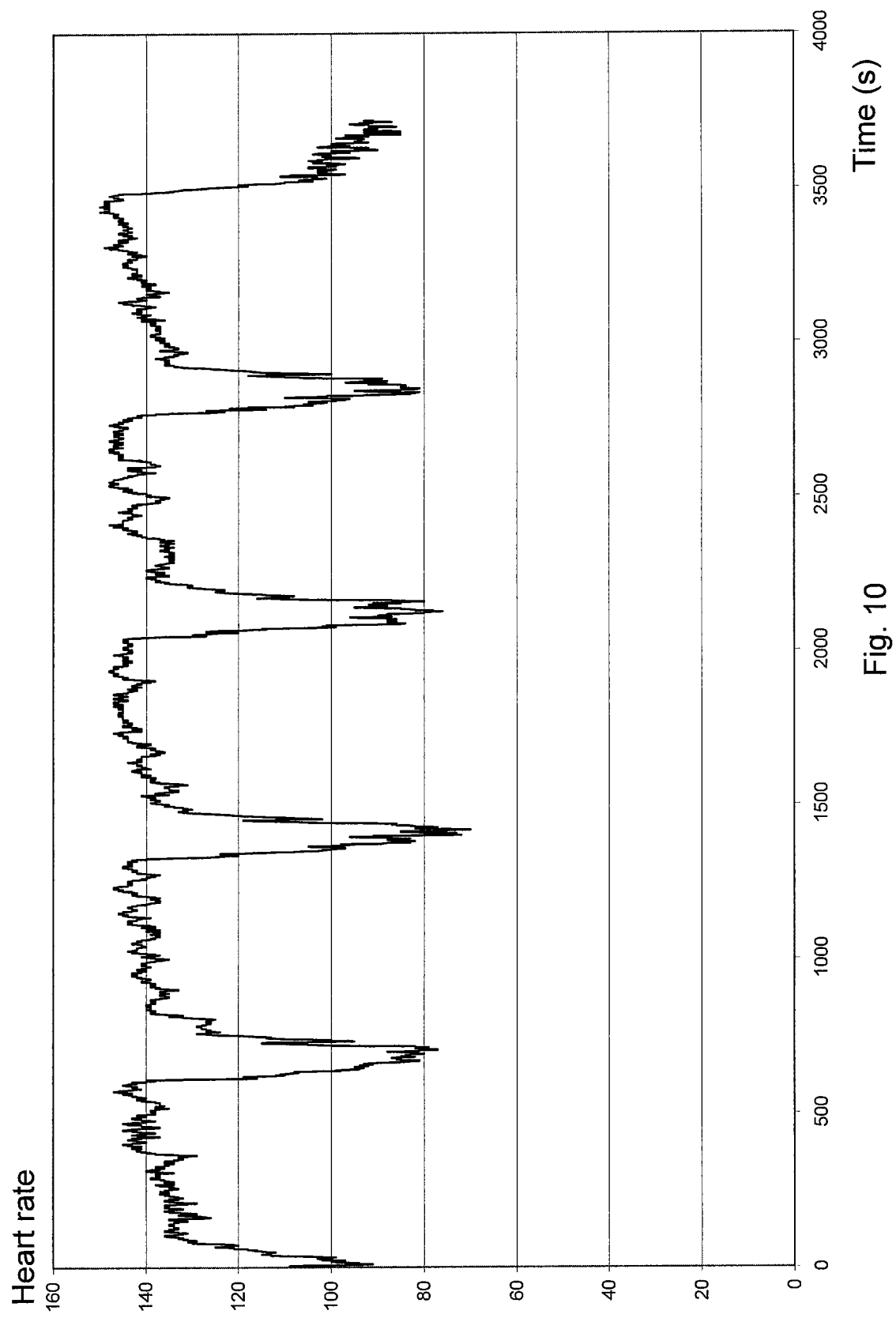
FIG. 10 is a diagram of heart rate of a human subject walking on a treadmill at alternating 10 minutes intervals of high load and 2 minutes intervals of rest.

FIG. 10 illustrates the results of a test of alternating periods of High load and periods of Rest. In the experiment 10 minutes of exercise (load High) is followed by rest (load Rest) for 2 minutes. This was repeated 5 times during the experiment. As in previous experiments the heart rate increased rapidly from a base rate of, in this case, about 90 bpm up to about 130 bpm and then slowly increased during the periods of exercise (High load). The slow increase in heart rate over time during periods of exercise was not significantly affected by the intermediate periods of rest The present embodiments provide an active-responsive cardiac pacing that mimics this natural change in heart rate during periods of exercise and increased subject activity. Hence, the pacing rate is according to the embodiments determined based on not only the current activity level of the subject but also of the length of the period of increased activity. The cardiac pacing of the embodiments will therefore more closely mimic the natural heart rhythm during periods of exercise as compared to the prior art solutions which solely determine the pacing rate based on the activity level but not on the length of the period of activity.

Figure 1:
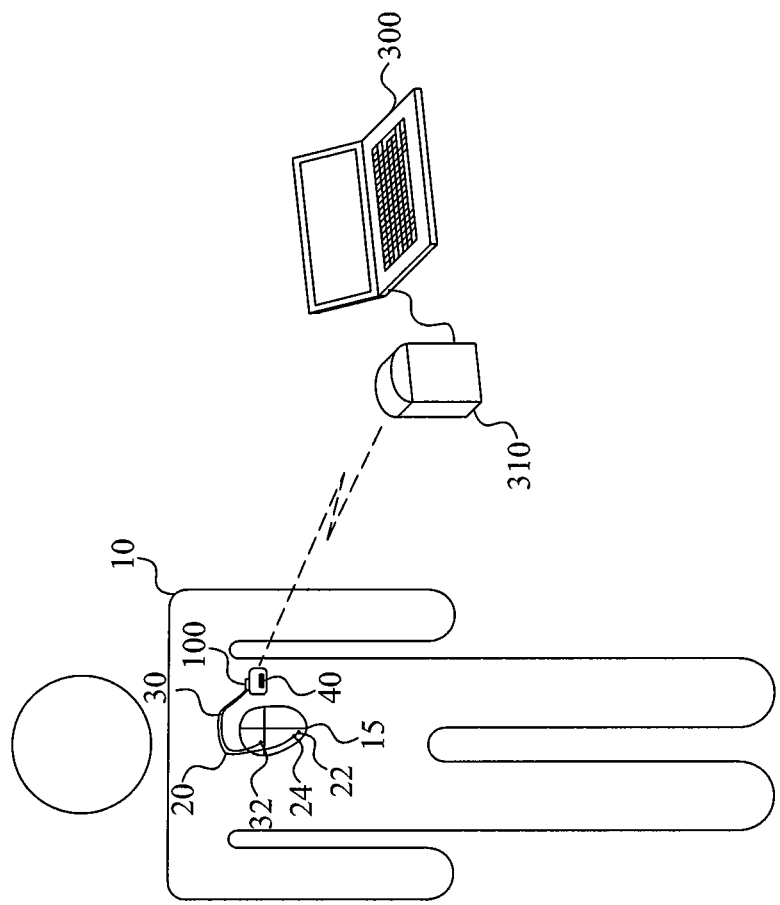
FIG. 1 is an overview of a human subject having an implantable medical device according to an embodiment.

FIG. 1 is a schematic overview of a subject, represented by a human subject 10 having an implantable medical device (IMD) 100 according to the embodiments. The IMD 100 is implanted in the subject 10 in order to provide pacing therapy to the subject's heart 15. The IMD 100 can be in the form of a pacemaker or an implantable cardioverter-defibrillator (ICD). The IMD 100 is, during operation in the subject's body, connected to an implantable medical lead or cardiac lead 20, 30 having at least one pacing electrode 22, 24, 32 arranged in or in connection with the subject's heart 15 to deliver pacing pulses to the heart 15 according to a pacing rate determined according to the embodiments by the IMD 100.

In FIG. 1, the IMD 100 has been exemplified as being connectable to a right ventricular (RV) lead 20 and a right atrial (RA) lead 30. An RV lead 20 is typically provided inside the right ventricle of the heart 15 and comprises one or more electrodes 22, 24 that can be used by the IMD 100 to apply pacing pulses to the right ventricle and/or sense electrical activity from the right ventricle. An RA lead 30 having at least one electrode 32 arranged in or in connection with the right atrium, can be used by the IMD 100 in order to provide atrial pacing and/or sensing. Instead of or as a complement to an RA lead, the IMD 100 can be connected to a left atrial (LA) lead. Furthermore, instead of or as a complement to the RV lead 20 the IMD 100 could be connected to a left ventricular (LV) lead. Such a LV lead is generally provided on the outside of the heart 15 typically in the coronary venous system, e.g. in a left lateral vein or a postero-lateral vein. The LV lead enables the IMD 100 to apply pacing pulses to the left ventricle and sense electrical activity from the left ventricle.

The particular implantable medical lead(s) which are connectable to the IMD 100 are not decisive for the present embodiments. Thus, the IMD 100 could be, in operation in the subject body, connected to a single implantable medical lead 20, 30 or multiple, i.e. at least two, implantable medical leads 20, 30. The relevant feature is that the IMD 100 is connectable to at least one implantable medical lead 20, 30 having at least one pacing electrode 22, 24, 32, which can be used to deliver pacing pulses to the heart 15.

FIG. 1 additionally illustrates a non-implantable data processing device 300, such as in the form of a programmer, a home monitoring device or a physician's workstation. The data processing device 300 comprises or is connected to a communication module or device 310 that is capable of wirelessly communicating with the IMD 100, preferably through radio frequency (RF) based communication or inductive telemetry. The data processing device 300 can then use the communication module 310 in order to interrogate the IMD 100 for diagnostic data recorded by the IMD 100 employing the electrodes 22, 24, 32 of the connected implantable medical lead(s) 20, 30. Furthermore, the data processing device 300 can be used to program the IMD 100, such as by setting one or more programmable operating parameters. According to the present embodiments, the data processing device 300 can in particular be used in order to program a base pacing rate, an activity pacing rate and an increase in pacing rate as a function of activity period length into the IMD 100.

The communication module 310 and the data processing device 300 can be separate devices as illustrated in FIG. 1, either wired connected or using a wireless connection, such as Bluetooth®, an infrared (IR) connection or an RF connection. In an alternative embodiment, the functionality and equipment of the communication module 310 can be housed within the data processing device 300.

The IMD 100 of the embodiments furthermore comprises or is connectable to an activity sensor 40 that is configured to generate a sensor signal that is representative of a current activity level of the subject 10. Various such implantable activity sensors 40 are known in the art and can be used according to the embodiments. For instance, U.S. Pat. No. 7,021,141 discloses an implantable accelerometer of beam-type that can be used as an activity sensor. Briefly, the accelerometer has a cantilever beam supported at one end and having an opposite free end with a longitudinal direction between the supported end and the free end. The beam is formed of a piezoelectric layer and a supporting layer. An inertial, sensing mass is mounted at the free end of the beam and is located eccentrically relative to the longitudinal direction of the beam. The accelerometer has a primary direction of sensibility to acceleration forces, and a secondary direction of sensitivity, which is orthogonal to the primary direction and in which the sensitivity is negligible. The secondary direction forms an angle relative to the longitudinal direction of the beam such that a line coinciding with a force proceeding through the center of gravity of the inertial mass, and which is directed in the secondary direction, also intersects the beam.

Another type of accelerometer that can be used as activity sensor 40 of the embodiments is disclosed in U.S. Pat. No. 6,466,821. The accelerometer is a multi-axis DC accelerometer that can be used to determine a subject's activity level.

An activity sensor 40 that can be used according to the embodiments is disclosed in U.S. Pat. No. 5,496,352 that is a piezoelectric accelerometer activity sensor. The sensor includes a thin film piezoelectric cell within a frame structure. A mass imposes a load based upon acceleration to apply lateral or transverse forces, which cause the generation of an electrical potential within the piezoelectric cell. This electric potential is representative of the subject's activity level.

U.S. Pat. No. 5,383,473 discloses a miniature, hybrid-mountable accelerometer-based physical activity sensor that can be used with an activity-responsive IMD 100. The sensor is constructed as a cantilever beam having a film of a piezoelectric polymer adhered to each surface of an electrically conductive substrate. The piezoelectric films are highly resistant to fracturing during manufacture and in use and they provide a strong output signal when stressed in response to bodily accelerations. The sensor is adapted to be mounted directly to an IMD 100.

The above presented activity sensors 40 should merely be seen as illustrative but non-limiting examples of activity sensors 40 that can be used by the activity-responsive IMD 100 of the embodiments 100. Hence, any implantable sensor that can generate a sensor signal representative of a current activity level of a subject 10 can be used according to the embodiments.

The activity sensor 40 could be mounted inside the housing of the IMD 100 and is thereby included in the IMD 100. Alternatively, the activity sensor 40 could be mounted on the outside of the IMD 100 and connected thereto through a connector to be further described herein. Also more remotely provided activity sensors 40 that are electrically connected to the IMD 100 through the connector can be used according to the embodiments. The activity sensor 40 could then be present on a connected implantable medical lead or be provided as a separate implantable unit.

Figure 2:
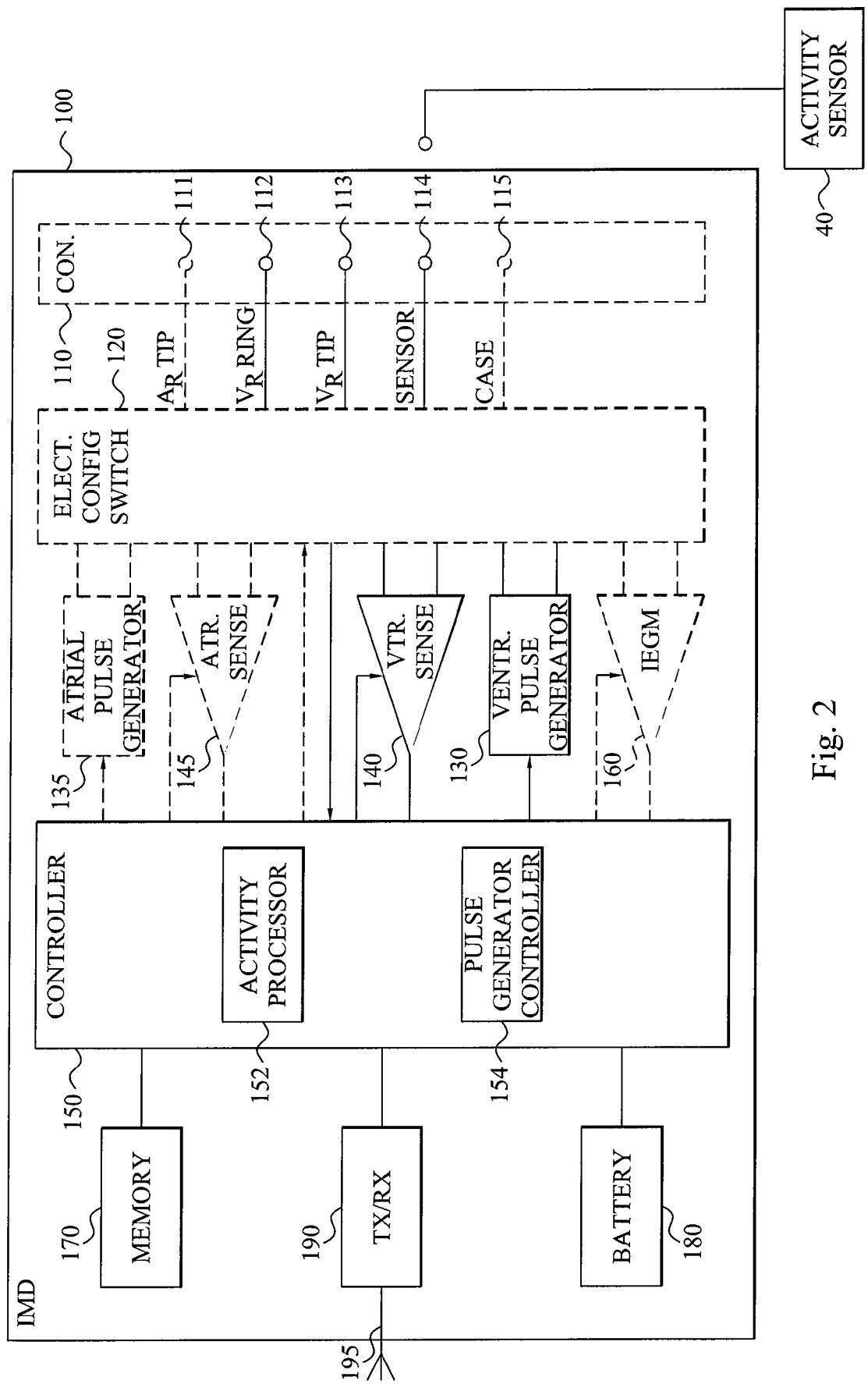
FIG. 2 is a schematic block diagram of an implantable medical device according to an embodiment.

FIG. 2 is a schematic block diagram of an activity-responsive IMD 100 according to an embodiment. The IMD 100 comprises a connector 110 having connector terminals 111-114 configured to be connected to matching electrode terminals of one or more implantable leads and optionally an implantable sensor 40. In FIG. 2, the connector 110 has been adapted to the particular lead configuration illustrated in FIG. 1. Hence, the connector 110 comprises, in this example, connector terminals 112, 113 configured to be electrically connected to the tip electrode 22 and ring electrode 24 of the RV lead 20 illustrated in FIG. 1. Correspondingly, the connector terminal 111 is configured to be electrically connected to the electrode 32 of the RA lead 30 in FIG. 1.

The connector 110 could also comprise one or more connector terminals 115 configured to be connected to one or more respective case electrodes, which are attached to or forming part of the housing of the IMD 100.

In an embodiment, the connector 110 furthermore comprises at least one connector terminal 114 connectable to an activity sensor 40. This activity sensor 40 is configured to generate a sensor signal representative of an activity level of a subject as previously discussed herein. Alternatively, the activity sensor 40 forms part of the IMD 100 and is thereby provided inside the housing of the IMD 100. In such a case, the activity sensor 40 can be directly connected to an activity processor 152, possibly through an electronic configuration switch 120. The connector terminal 114 can then be omitted.

The actual number and type of connector terminals 111-115 of the connector 110 depend on the particular type of activity sensor 40, the particular lead configuration, if any case electrodes are available and if the activity sensor 40 forms part of the IMD 100 or is connected thereto through the connector 110. Thus, the particular terminal configuration of FIG. 2 should merely be seen as an illustrative but non-limiting example.

The IMD 100 comprises an activity processor 152 connected to the connector 110, possibly through an optional electronic configuration switch 120, or directly to the activity sensor 40. The activity processor 152 thereby receives the sensor signal from the activity sensor 40 optionally through the connector 110 and the optional switch 120. The activity processor 152 processes the sensor signal in order to determine a current activity level of the subject based on the sensor signal. The particular signal processing conducted by the activity processor 152 generally depends on the type of activity sensor 40. Thus, the current activity level of the subject could be determined by the activity processor 152 based on the amplitude of the (electric) sensor signal, the frequency of the (electric) sensor signal or the pulse width of the sensor signal as illustrative examples. The particular processing is not relevant as long as the activity processor 152 is capable of determining or at least estimating a current activity level of the subject based on the sensor signal.

The activity processor 152 is further configured to determine a time period during which the current activity level determined based on the sensor signal has exceeded a first threshold level. Thus, the activity processor 152 determines the time period during which the subject exercises at least a minimum activity level as defined by the first threshold level. The first threshold level could be stored in a memory 170 connected to and available to the activity processor 152.

The time period of sufficient high subject activity can be determined by comparing the value of each sensor signal sample with the first threshold value, possible after filtering, such as averaging a selected number of consecutive sensor signal samples to combat noise and non-physiological and temporary odd sample values that are not due to changes in activity level of the subject. The activity processor 152 could then start a clock or timer once a first such (filtered or average) sensor signal sample represents a current activity level that exceeds the activity level represented by the first threshold value. The clock or timer continues running as long as subsequent (filtered or average) sensor signal samples indicate a continuous activity level above the threshold level. In an alternative approach, the activity processor 152 does not need to have access to a clock or timer. In clear contrast, the time period is determined by counting the number of consecutive (filtered or average) sensor signal samples that represent an activity level above the first threshold level. This number could then be used directly as a representation of the time period or it is converted into a time value based on the sampling frequency of the activity sensor 40.

The IMD 100 also comprises a pulse generator 130, 135 connected to the connector 110, optionally through the electronic configuration switch 120. The pulse generator 130, 135 is configured to generate pacing pulses to be applied to at least one pacing electrode of a connected implantable medical lead. The pulse generator could be a ventricular pulse generator 130 if the generated pacing pulses are to be applied to a ventricle of the heart using a connected RV and/or LV lead. Alternatively, the pulse generator could be an atrial pulse generator 135 if the generated pacing pulses are to be applied to an atrium of the heart using a connected RA and/or LA lead. It is also possible for the IMD 100 to comprise both a ventricular pulse generator 130 and an atrial pulse generator 135.

The ventricular and atrial pulse generators 130, 135 of the IMD 100 may include dedicated, independent pulse generators, multiplexed pulse generators, or shared pulse generators. The pulse generators 130, 135 are controlled by a pulse generator controller 154 via appropriate control signals, respectively, to trigger or inhibit the stimulating pulses.

The above-mentioned pulse generator controller 154 is connected to and controls the pulse generator 130, 135 to generate pacing pulses at a defined pacing rate that is determined by the pulse generator controller 154. According to the embodiments, the pulse generator controller 154 is configured to determine the pacing rate to be used by the pulse generator 130, 135 based on the current activity level of the subject as determined by the activity processor 152 based on the sensor signal and based on the length of the time period during which the current activity level has exceeded the first threshold level as determined by the activity processor 152.

The IMD 100 thereby provides an activity-adaptive pacing rate where the pacing rate is determined based not only on the current activity level of the subject but also on the length of the period of subject activity.

The length of the period of activity or exercise by the subject is the period during which the subject is exercising and reaching an activity that exceeds a minimum activity as defined by the first threshold level. Thus, if the subject is active but not exercising at sufficient high level to exceed the minimum activity the length of any (low) activity period is typically not regarded by the pulse generator controller 154. Thus, the subject has to reach at least a minimum activity level before the pacing rate of the IMD 100 needs to be adapted based also on the length of the period of activity.

The particular first threshold level could be a fixed level that is determined to be subject-generic and applied to all IMD subjects. However, since the base heart rate at rest, the maximum heart rate and how rapidly the heart rate increases in connection with an increase in activity are generally subject-specific, the first threshold value is preferably determined for the particular subject by his/her physician and downloaded into the IMD 100 using the data processing device 300 illustrated in FIG. 1. The subject can then undergo different exercise tests, similar to the ones discussed above in connection with FIGS. 6-10, in order to identify a suitable subject-specific value for the first threshold level and over which the time period of activity affects the heart rate.

Once such a first threshold level has been determined for the subject, it can be downloaded to the IMD 100 and received by a receiver having a connected antenna 195 or by a transceiver (TX/RX) 190 having both receiving and transmitting circuits. The received notification of the first threshold level is then entered in the memory 170, where it can be used by the activity processor 152.

The determination of the pacing rate at which pacing pulses are generated by the pulse generator 130, 135 and applied to the subject's heart based on the length of the time period of activity and exercise means that the IMD 100 provides an adaptive and dynamic determination of the pacing rate. Thus, as the length of the time period of activity and exercise increases the pacing rate is preferably updated by the pulse generator controller 154 even though the activity level of the subject may remain substantially the same during the period of activity and exercise. This means that the pulse generator controller 154 preferably determines a current optimal pacing rate for the subject as a function ($f(\ldots)$) of these two input parameters, the current activity level ($L_A$) and the length of the time period of activity ($T_A$):

Pacing rate=$f(L_A,T_A)$

Hence, as time progresses and the subject still exercises and has an activity level exceeding the first threshold level the pulse generator controller 154 preferably dynamically updates the pacing rate of the pulse generator 130, 135 and more preferably increases the pacing rate.

The pulse generator controller 154 preferably dynamically updates the pacing rate over time as mentioned in the foregoing. In such a case, the activity processor 152 could then determine a current activity level and update the time period of activity periodically. For instance, the activity processor 152 could determine an updated current activity level and updated time period of activity every minute, every second minute or every five minutes as non-limiting but illustrative examples. Also more frequent updates are possible such as multiple times per minute. However, it is generally sufficient to use a less frequent update and which additionally does not drain the power supply of the IMD 100, i.e. a battery 180, as quickly as more frequent updates.

The pulse generator controller 154 could thereby update the pacing rate at the same frequency as the activity processor 152 uses to determine updated current activity levels and updated time periods. It is also possible to use a less frequent update of the pacing rate by the pulse generator controller 154 than for the activity processor 152. For instance, the pulse generator controller 154 could use an average of the multiple current activity level values together with the length of the updated time period of activity when determining an updated pacing rate.

The increase in pacing rate over time due to the length of the period of activity could, as discussed in connection with FIGS. 6-10, be in the form of X bpm/minute, where X is a positive number. In such a case, the slow, dynamic increase in pacing rate by the pulse generator controller 154 based on the length of the period of activity could be to increase the pacing rate with X pacing pulses per minute.

The update of pacing rate based on the length of the period of activity of the embodiments can be used together with traditional rate-responsive IMDs that determine suitable stimulation or pacing rate based (solely) on the current activity level of the subject. Such a rate-responsive pacing could then increase the pacing rate in steps so that a first pacing rate is used within a first given activity level interval, a second higher pacing rate is used within a second given activity level interval and so forth. A further rate-responsive approach is to have access to one or multiple rate-slopes that define a linear increase in pacing rate as a function of current activity level. The particular slope then defines how much the pacing rate should be increased for a given increase in activity level. Examples of such rate-responsive approaches are disclosed in U.S. Pat. Nos. 4,940,052; 4,922,907; 5,040,534; 5,074,302 and 5,423,867.

Such rate-responsive approaches that adapt the pacing rate based on the activity level can then be complemented with a further adaptivity of the pacing rate based on not only the current activity level (such as in steps or linearly) but also on the length of the period of activity. This means that if the subject is exercising during some time and increases his or her activity level during the exercise period, the pacing rate is preferably dynamically updated both in response to the increase in activity level and also in response to the increasing length of the period of exercise.

In a particular embodiment, the activity processor 152 is configured to calculate an activity parameter that is used by the pulse generator controller 154 when determining and updating the pacing rate of the pulse generator 130, 135. The activity processor 152 could calculate this activity parameter by integrating the sensor signal over time if the current activity level exceeds the first threshold level. The pulse generator controller 154 then controls the pulse generator 130, 135 to generate pacing pulses at a pacing rate determined by the pulse generator controller 154 based on the current activity level and the activity parameter.

By integrating the sensor signal over time during the period at which the activity level of the subject exceeds the first threshold level, the activity parameter will increase when the subject continues to exercise at least the first threshold level. This then preferably implies that the pulse generator controller 154 controls the pulse generator 130, 135 to use a higher pacing rate when the activity parameter has a first value as compared to when the activity parameter has a lower value and if the current activity level is the same in both cases.

If the subject stops exercising or reduces his/her activity level to a very low activity level, i.e. below the first threshold level, the activity processor 152 preferably resets the activity parameter. Thus, the integration of the sensor signal over time preferably only continues as long as the current activity level of the subject exceeds the first threshold level. If the current activity level drops below the first threshold level, the activity processor 152 stops integrating the sensor signal and instead resets the activity parameter.

The resetting of the activity parameter in connection with the subject resting or only having a low activity level can be performed according to various embodiments. In a first approach, the activity processor 152 simply sets the activity parameter to a starting value, i.e. zero. This then means that the dynamic adaptation of the pacing rate in response to the length of the time period of activity no longer takes place since the subject is not active enough to benefit from such a slow increase in pacing rate any longer. However, if the subject would once more increase its activity level to anew exceed the first threshold level, the activity processor 152 preferably reassumes the calculation of the activity parameter to thereby enable a dynamic adaptation of the pacing rate based on the length of the period of subject activity.

In another approach the activity processor 152 does not directly set the activity parameter to the starting value, e.g. zero, but rather resets the activity parameter step by step depending on a length of a time period for which the current activity level is below the first threshold value. For instance, the activity processor 152, in an illustrative example, halves the activity parameter value once the current activity level drops below the first threshold value, and then once more halves the remaining activity parameter after, for example, one minute of resting or activity below the first threshold value and then setting the activity parameter to zero after, for example, two minutes of resting or activity below the first threshold value.

This approach could be more physiological relevant if the subject very briefly rests for just a few seconds before resuming his/her exercise. By then reducing the activity parameter value to a value larger than the starting value, e.g. zero, means that the dynamic adaptation of the pacing rate based on the activity parameter will come into effect sooner following the resumed exercise as compared to if the activity parameter value would be reset to zero directly at the start of the short resting period.

The above presented examples of how the resetting could be done in steps should merely be seen as illustrative examples. The particular approach taken by the activity processor 152 could be configured by the subject's physician and downloaded into the IMD 100 through the transceiver 190 and antenna 195.

In a particular embodiment, the pulse generator controller 154 is configured to control the pulse generator 130, 135 to operate at one of multiple predefined pacing rates. These predefined pacing rates are then adapted to different activity levels of the subject. For instance, the pulse generator controller 154 could use two different pacing rates, a base pacing rate that is used during rest and low activity levels and an activity pacing rate that is used when the subject is exercising, where the activity pacing rate is higher than the base pacing rate. In such a case, the pulse generator controller 154 preferably controls the pulse generator 130, 135 to generate pacing pulses according to the base pacing rate as long as the current activity level as determined by the activity processor is equal to or below a second threshold level. However, once the current pacing rate exceeds the second threshold level the pulse generator controller 154 switches to controlling the pulse generator 130, 135 to instead use the activity pacing rate. In this example, the second threshold level at which pacing rates are switched between the base pacing rate to the activity pacing rate could be equal to or be lower than the first threshold level above which time of activity becomes relevant for adjusting the pacing rate.

The pulse generator controller 154 is then configured to control the pulse generator 130, 135 to increase the pacing rate above the selected activity pacing rate based on the length of the time period of activity above the first threshold level. Thus, when the subject is starting to exercise his/her activity level increases from a base level at which the pulse generator controller uses the base pacing rate up to and exceeding the second threshold level. At this point the pulse generator controller 154 switches to instead control the pulse generator 130, 135 to use the activity pacing rate. Once the activity level exceeds the first threshold level (which could be the same as or different, typically higher, than the second threshold level), the activity processor 152 could start to calculate the activity parameter. The pulse generator controller 154 thereby slowly increases the pacing rate above the activity pacing rate as time passes and the subject is still at an activity level exceeding the first threshold value, i.e. the activity parameter value increases.

For instance and with the results presented in FIG. 7, the base pacing rate could be represented by 80 bpm and the activity pacing rate is 130 bpm. The pacing rate is then increased with 0.5 bpm per minute of exercise above a defined threshold level.

Figure 5:
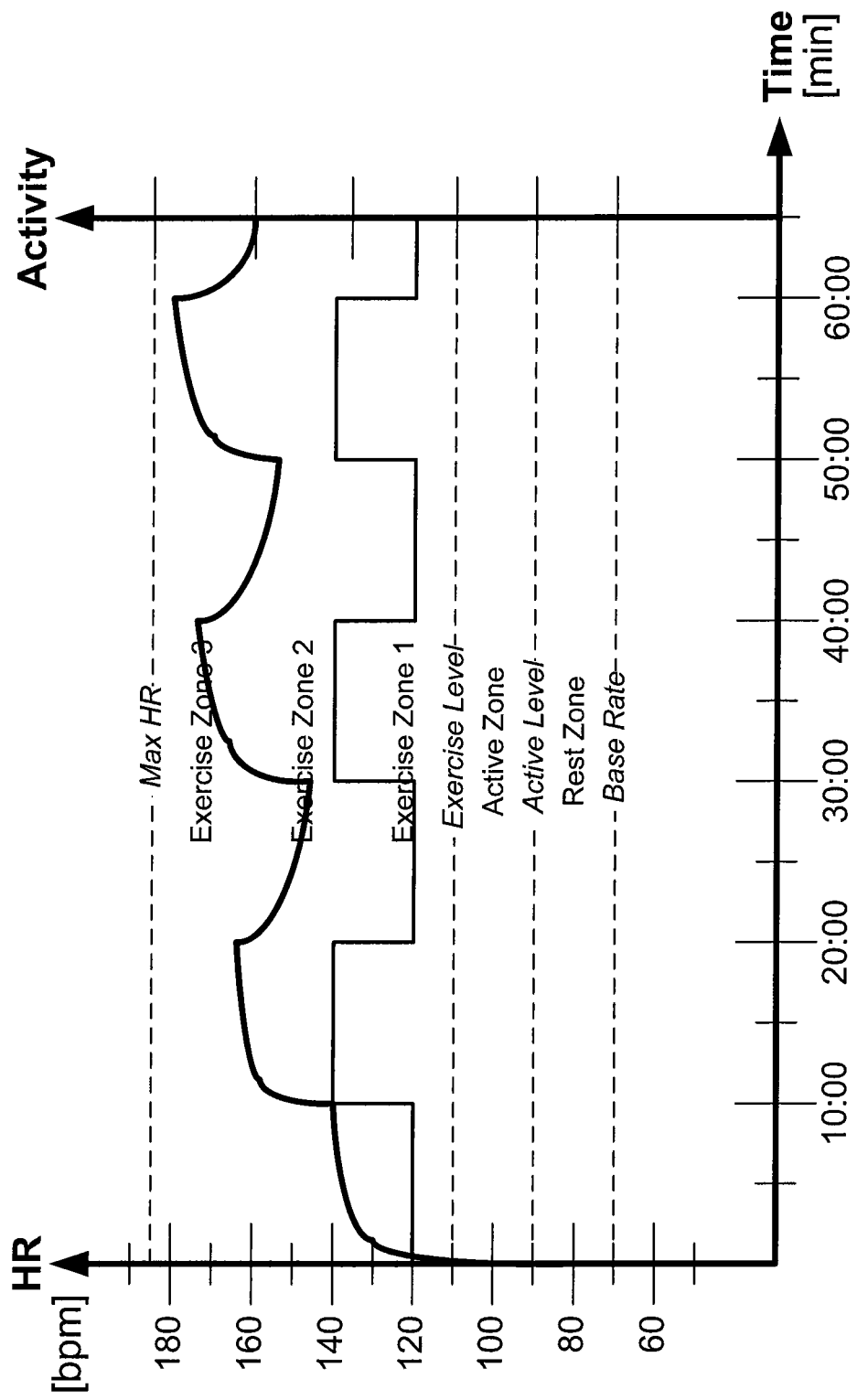
FIG. 5 is a diagram schematically illustrating operation of an implantable medical device according to an embodiment.

With reference to FIG. 5, this approach can be extended to the case with more than two predefined pacing rates and using different threshold levels. For instance, the base pacing rate is used when the current activity level does not exceed the second threshold level, i.e. is in the rest zone of FIG. 5. Correspondingly, an active level pacing rate is used when the current activity level exceeds the second threshold level but does not exceed the first threshold level and therefore is in an active zone. An exercise pacing rate is used when the current activity level exceeds the first threshold level and is in an exercise zone. This exercise zone can furthermore be divided into multiple exercise zones as indicated in FIG. 5. An extension of this case is to have a linear relationship between activity level and pacing rate as previously mentioned herein.

The generator controller 154 then increases the pacing rate from the exercise pacing rate based on the length of the time period of activity.

FIG. 5 illustrates the current activity level of the subject with the thin full line and the resulting heart rate with the thick full line. The present embodiments are then able to control the pacing rate to mimic this natural change in heart rate during periods of exercise.

The particular values of the multiple predefined pacing rates are advantageously set by the subject's physician and stored in the memory 170 of the IMD 100 together with the values of the threshold levels mentioned in the foregoing.

In these embodiments, the current activity level is employed by the pulse generator controller 154 to determine which predefined pacing rate to currently use for the subject. The length of the time period of activity, such as represented by the activity parameter, is then used to control the dynamic increase in the pacing rate relative to the selected predefined pacing rate.

As was shown in connection with FIGS. 7 and 8, the slow increase in heart rate over time typically depends on the activity level of the subject. Thus, in FIG. 7 with a higher activity level (load High) the heart rate increase over time was higher than in FIG. 8 with a lower activity level (load Low), i.e. 0.5 bpm/minute as compared to 0.1 bpm/minute.

In an embodiment, the pulse generator controller 154 therefore determines the increase in pacing rate over time based on the current activity level of the subject. For instance, the pulse generator controller 154 could determine or use a first increase in the pacing rate in response to the length of the time period of activity if the current activity level exceeds the first threshold level. However, if the current activity level not only exceeds the first threshold level but also a third, higher threshold level, the pulse generator controller 154 is configured to determine or use a second, larger increase in the pacing rate in response to the length of the time period of activity.

The increase in pacing rate over time as the subject is continuing to exercise can preferably only continue until the pacing rate reaches a defined maximum pacing rate (see FIG. 5). Thus, if the subject has exercised for quite a long period of time and the pulse generator controller 154 has slowly increased the pacing rate over time and reached the maximum pacing rate, the pulse generator controller 154 does not continue to increase the pacing rate further even if the subject continues to exercise at an activity level above the first threshold level. The actual value of this maximum pacing rate is preferably subject-specific and stored in the memory 170. A reason for limiting the pacing rate could be to prevent various tachycardia conditions and preventing any (false) detection of arrhythmia by the IMD 100 since such arrhythmia detection are typically based on the current heart rate of the subject.

The activity sensor 40 used by the embodiments could be operating to continuously monitor the activity level of the subject. Alternatively, the activity sensor 40 is controlled, such as by a general controller 150 of the IMD 100, to periodically record the sensor signal representing the activity level of the subject. In a particular approach, the activity sensor 40 is controlled to periodically record the sensor signal as long as the current activity level of the subject is below any of the above mentioned threshold levels. However, once the activity levels has increased above the first threshold level or the second threshold level, the activity sensor 40 could switch from periodically recording the sensor signal at a first periodicity to continuously recording the sensor signal or recording the sensor signal at a second periodicity, i.e. more often than during periods of no or low activity. This generally saves power supply of the IMD 100 by merely recording and processing the sensor signal when the activity is high enough to cause a change in the applied pacing rate.

The IMD 100 may optionally also comprise circuits for sensing electrical activity of the heart. Such circuits can be in the form of a ventricular sensing circuit 140 and/or an atrial sensing circuit 145. The ventricular and atrial sensing circuits 140, 145 of the IMD 100 may include dedicated sense amplifiers, multiplexed amplifiers, or shared amplifiers. The electronic configuration switch 120 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 140, 145 preferably employs one or more low power, precision amplifiers with programmable gain and/or automatic gain control, band-pass filtering, and a threshold detection circuit, as known in the art, to selectively sense the cardiac signal of interest.

The outputs of the ventricular and atrial sensing circuits 140, 145 are connected to the controller 150, which, in turn, is able to trigger or inhibit the ventricular and atrial pulse generators 130, 135, respectively, in a demand fashion in response to the absence or presence of cardiac activity in the appropriate chambers of the heart.

The controller 150 of the IMD 100 is preferably in the form of a programmable microcontroller 150 that controls the operation of the IMD 100. The controller 150 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 150 is configured to process or monitor input signals as controlled by a program code stored in a designated memory block. The type of controller 150 is not critical to the described implementations. In clear contrast, any suitable controller may be used that carries out the functions described herein. The use of microprocessor-based control circuits for performing timing and data analysis functions are well known in the art.

Furthermore, the controller 150 is also typically capable of analyzing information output from the sensing circuits 140, 145 to determine or detect whether and to what degree tissue capture has occurred and to program a pulse, or pulse sequence, in response to such determinations. The sensing circuits 140, 145, in turn, receive control signals over signal lines from the controller 150 for purposes of controlling the gain, threshold, polarization charge removal circuitry, and the timing of any blocking circuitry coupled to the inputs of the sensing circuits 140, 145 as is known in the art.

The optional electronic configuration switch 120 includes a plurality of switches (not shown) for connecting the desired connector terminals 111-115 to the appropriate I/O circuits, thereby providing complete electrode programmability. Accordingly, the electronic configuration switch 120, in response to a control signal from the controller 150, determines the polarity of the stimulating pulses by selectively closing the appropriate combination of switches as is known in the art.

While a particular multi-chamber device is shown in FIG. 2, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination.

The IMD 100 could also comprise an intracardiac electrogram (IEGM) processor 160 connected to the connector 110 and configured to generate an IEGM signal based on electrical activity of the heart sensed by at least one sensing (and pacing) electrode connected to the connector 110. The IMD 100 additionally includes a battery 180 that provides operating power to all of the circuits shown in FIG. 2.

In FIG. 2, the activity processor 152 and the pulse generator controller 154 have been illustrated as being run by the controller 150. These units 152, 154 can then be implemented as a computer program product stored in the memory 170 and loaded and run on a general purpose or specially adapted computer, processor or microprocessor, represented by the controller 150 in FIG. 2. The software includes computer program code elements or software code portions effectuating the operation of the units 152, 154. The program may be stored in whole or part, on or in one or more suitable computer readable media or data storage means that can be provided in an IMD 100.

In an alternative approach, the units 152, 154 are implemented as hardware circuits in the IMD 100, preferably connected to the controller 150, such as in the form of special purpose circuits, such as ASICs (Application Specific Integrated Circuits).

The embodiments not only provide a cardiac pacing that is physiologically adaptive during periods of exercise and activity of a subject. Improvements in the adaptive heart rate response may also enable a lower base rate setting, which may reduce the long-term cardiac mechanical load and ischemia risk in subjects having an implantable medical device of the embodiments. It is further expected that the embodiments, which provide a cardiac pacing that mimics the natural pattern of rate increase during exercise, may reduce the risk of ischemia. Subjects suffering from severe chronotropic incompetence would benefit from an improved, i.e. a more physiological rate response pacing according to the embodiments, by increasing the exercise tolerance and quality of life for this group of subjects.

Figure 3:
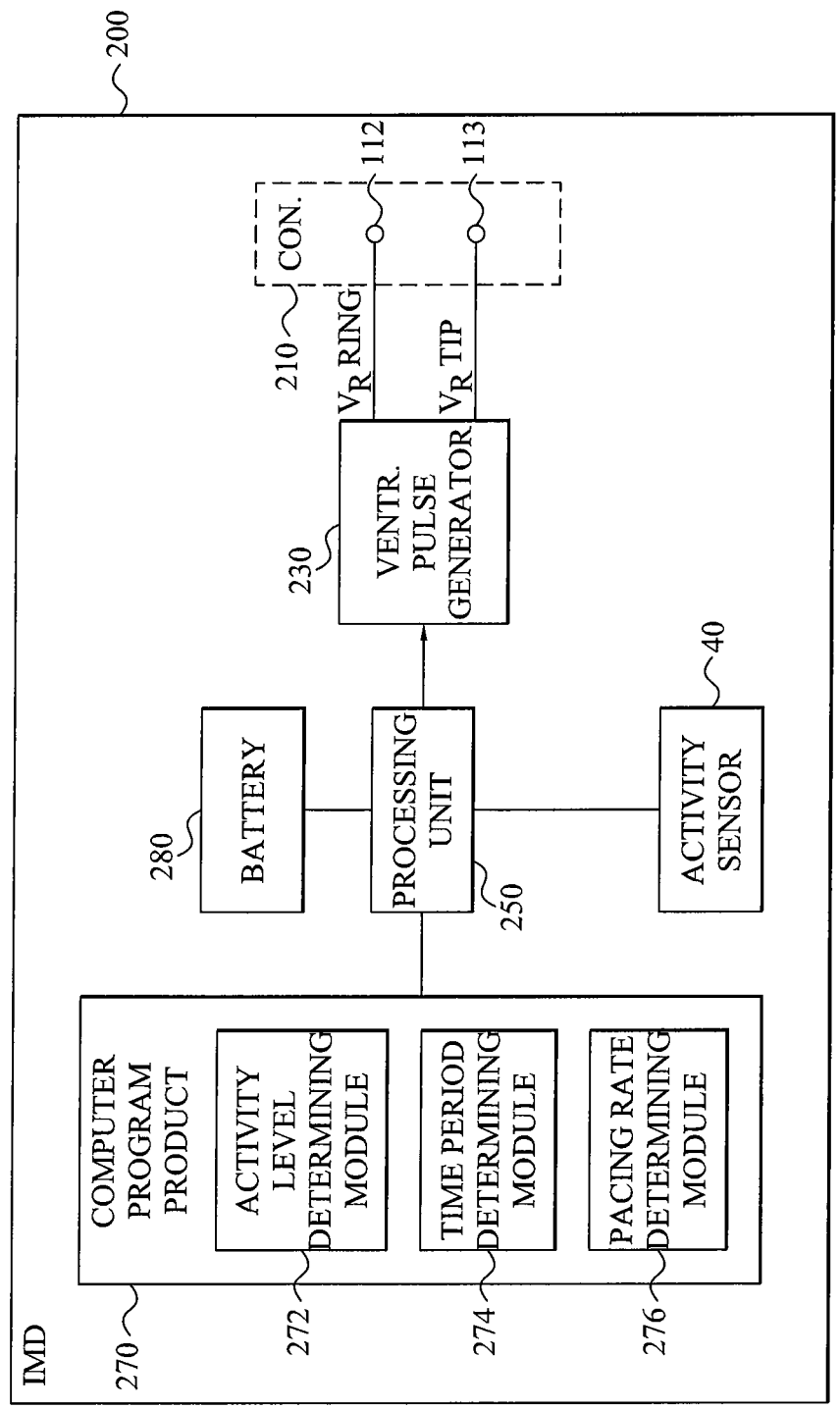
FIG. 3 is a schematic block diagram of an implantable medical device according to another embodiment.

FIG. 3 is a schematic block diagram of another embodiment of an activity-responsive implantable medical device 200. This embodiment of the IMD 200 comprises the previously discussed connector 210 with connector terminals 112, 113 and pulse generator 230. In this particular example, the IMD 200 comprises the activity sensor 40. Such an approach is also possible with the IMD 100 illustrated in FIG. 2. Furthermore, in an alternative embodiment of the IMD 200 in FIG. 3, the activity sensor 40 could be connected to the IMD 200 through the connector 210, such as provided on a cardiac lead. In either case, in an embodiment, the connector 210 is connectable to a ventricular cardiac lead, such as an RV lead. Hence, the pulse generator 230 has been exemplified as a ventricular pulse generator 230 and the connector 210 comprises connector terminals 112, 113 for connection to an RV lead.

In this embodiment, the IMD 200 comprises a processing unit 250, such as a DSP (Digital Signal Processor) or CPU (Central Processing Unit), that substantially operates similar to the controller of FIG. 2. The processing unit 250 can be a single unit or a plurality of units for performing different steps of the method described herein. The IMD 200 also comprises at least one computer program product 270 in the form of a non-volatile memory, for instance an EEPROM (Electrically Erasable Programmable Read-Only Memory), a flash memory or a disk drive. The computer program product 270 comprises a computer program, which comprises code means 272-276 which when run on the IMD 200, such as by the processing unit 250, causes the IMD 200 to perform the steps of the method described herein. Hence, in an embodiment the code means 272-276 in the computer program comprises an activity level determining module 272 for determining a current activity level for the subject based on the sensor signal from the activity sensor 40. The code means 272-276 also comprises a time period determining module 274 for determining a time period during which the current activity level as determined by the activity level determining module 272 has exceeded a first threshold level. A pacing rate determining module 276 determines a pacing rate for the pulse generator 230 to generate pacing pulses based on the current activity level as determined by the activity level determining module 272 and the length of the time period determined by the time period determining module 274.

Thus, the present embodiment can easily be implemented in software together with traditional hardware circuits of IMDs.

Figure 4:
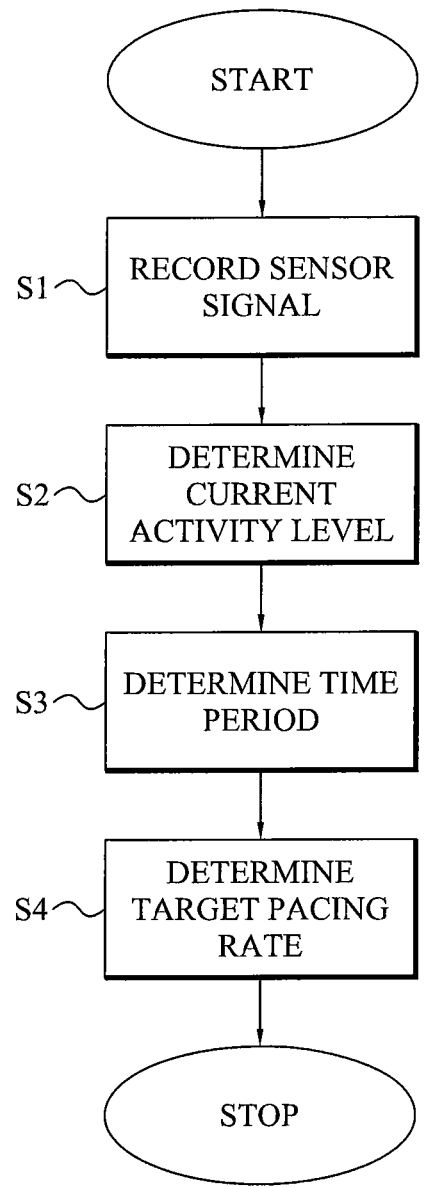
FIG. 4 is a flow diagram of an activity-responsive pacing method according to an embodiment.

FIG. 4 is a flow diagram of an activity-responsive pacing method according to an embodiment. The method starts in step S1 where a sensor signal representative of an activity level of a subject is recorded. The sensor signal is used in step S2 to determine a current activity level for the subject. A following step S3 determines a time period during which the current activity level determined in step S2 has exceeded a first threshold level. Finally, step S4 determines a target pacing rate for the subject based on the current activity level determined in step S2 and the length of the time period determined in step S3.

The method then ends. In a typical embodiment, the loop of steps S1 to S4 are repeated multiple times to dynamically adjust the target pacing rate based not only on the current activity level but also based on the progressing time of subject activity.

The time period of step S3 can be determined by calculating the activity parameter as previously disclosed herein. In such a case, the target pacing rate is determined in step S4 based on the current activity level and the activity parameter.

If the current activity level falls below the first threshold level the method preferably also comprises resetting the activity parameter either directly or by reducing the value of the activity parameter step by step depending on how long the subject has been resting or at least being active at an activity level below the first threshold value.

In a particular embodiment step S4 involves switching between a base pacing rate to an activity or exercise pacing rate when the current activity level exceeds a second threshold level. The pacing rate is then dynamically adjusted, i.e. increased, relative to the activity pacing rate based on the length of the time period determined in step S3. The particular increase in pacing rate in response to the length of the time period is preferably based on the current activity level. Hence, a first increase in pacing rate is determined if the current activity level exceeds the first threshold value but does not exceed a third, higher threshold value. However, if the current activity level exceeds the third threshold value a second, larger increase in pacing rate is determined in response to the length of the time period. In this case, the relevant time period is the length of the time period during which the current activity level determined based on the sensor signal has exceed not only the first threshold level but also the third threshold level.

A previously present herein, the increase in pacing rate is preferably not performed any further once the pacing rate has reached a defined maximum pacing rate.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An activity-responsive implantable medical device comprising:
   a connector connectable to an implantable medical lead having at least one pacing electrode;
   a pulse generator connected to the connector and configured to generate pacing pulses to be applied to the at least one pacing electrode;
   an activity processor configured to receive a sensor signal representative of an activity level of a subject from an activity sensor and determine a current activity level of the subject based on the sensor signal; and
   a pulse generator controller connected to the pulse generator and configured to control the pulse generator to generate the pacing pulses;
   wherein the activity processor is further configured to directly determine a time period during which the current activity level determined based on the sensor signal has exceeded a first threshold level; and
   wherein the pulse generator controller is configured to control the pulse generator to generate pacing pulses at a pacing rate determined based on the current activity level and directly based on a length of the time period such that the pacing rate=f($L_A$, $T_A$), wherein $L_A$ is the current activity level and $T_A$ is the length of the time period.

2. The activity-responsive implantable medical device according to claim 1, wherein
   the activity processor is configured to calculate an activity parameter by integrating the sensor signal over time if the current activity level exceeds the first threshold level; and
   the pulse generator controller is configured to control the pulse generator to generate pacing pulses at the pacing rate determined based on the current activity level and the activity parameter.

3. The activity-responsive implantable medical device according to claim 2, wherein the activity processor is configured to reset the activity parameter if the current activity level falls below the first threshold value.

4. The activity-responsive implantable medical device according to claim 3, wherein the activity processor is configured to reset the activity parameter by reducing a value of the activity parameter step by step depending on a length of a time period during which the current activity level is below the first threshold value.

5. The activity-responsive implantable medical device according to claim 1, wherein
the pulse generator controller is configured to control the pulse generator to switch from generating pacing pulses at a base pacing rate to an activity pacing rate when the current activity level determined by the activity processor based on the sensor signal exceeds a second threshold level, the activity pacing rate is higher than the base pacing rate; and
the pulse generator controller is configured to control the pulse generator to increase the pacing rate of generating the pacing pulses from the activity pacing rate based on the length of the time period.

6. The activity-responsive implantable medical device according to claim 5, wherein the pulse generator controller is configured to determine a first increase in pacing rate in response to the length of the time period if the current activity level as determined by the activity processor exceeds the first threshold level and determine a second, larger increase in pacing rate in response to the length of the time period if the current activity level as determined by the activity processor exceeds a third threshold level.

7. The activity-responsive implantable medical device according to claim 1, wherein the pulse generator controller is configured to control the pulse generator to increase the pacing rate of generating the pacing pulses from the activity pacing rate but not above a maximum pacing rate based on the length of the time period.

8. The activity-response implantable medical device according to claim 1, wherein the activity-responsive implantable medical device comprises the activity sensor.

9. The activity-response implantable medical device according to claim 1, wherein the connector is connectable to the activity sensor and the activity processor is connected to the connector.

10. An activity-responsive implantable medical device comprising:
a connector connectable to an implantable medical lead having at least one pacing electrode;
a pulse generator connected to the connector and configured to generate pacing pulses to be applied to the at least one pacing electrode;
a processing unit; and
a computer program product comprising computer readable code means, which when executed by the processing unit causes the processing unit to:
determine a current activity level of a subject based on a sensor signal representative of an activity level of the subject and received from an activity sensor;
directly determine a time period during which the current activity level has exceeded a first threshold level; and
determine a pacing rate for the pulse generator to generate the pacing pulses based on the current activity level and directly on a length of the time period such that the pacing rate=$(L_A, T_A)$, wherein $L_A$ is the current activity level $T_A$ the length of the time period.

11. An activity-responsive pacing method comprising:
recording a sensor signal representative of an activity level of a subject; and
determining a current activity level of the subject based on the sensor signal, wherein:
directly determining a time period during which the current activity level determined based on the sensor signal has exceeded a first threshold level; and
determining a target pacing rate for the subject based on the current activity level and a length of the time period.

12. The activity-responsive pacing method according to claim 11, wherein
directly determining the time period comprises calculating an activity parameter by integrating the sensor signal over time if the current activity level exceeds the first threshold level; and
determining the target pacing rate comprises determining the target pacing rate for the subject based on the current activity level and the activity parameter.

13. The activity-responsive pacing method according to claim 12, further comprising resetting the activity parameter if the current activity level falls below the first threshold value.

14. The activity-responsive pacing method according to claim 13, further comprising resetting the activity parameter comprises resetting the activity parameter by reducing a value of the activity parameter step by step depending on a length of a time period for which the current activity level is below the first threshold value.

15. The activity-responsive pacing method according to claim 11, further comprising:
switching from a base pacing rate to an activity pacing rate when the current activity level exceeds a second threshold level, the activity pacing rate is higher than the base pacing rate; and
increasing the pacing rate from the activity pacing rate based on the length of said time period.

16. The activity-responsive pacing method according to claim 15, further comprising:
determining a first increase in pacing rate in response to the length of the time period if the current activity level exceeds the first threshold level; and
determining a second, larger increase in pacing rate in response to the length of the time period if the current activity level exceeds a third threshold level.

17. The activity-responsive pacing method according to claim 15, wherein increasing the pacing rate comprises increasing the pacing rate of generating the pacing pulses from the activity pacing rate but not above a maximum pacing rate based on the length of the time period.

* * * * *